(12) United States Patent
Wojcik et al.

(10) Patent No.: US 9,820,703 B2
(45) Date of Patent: Nov. 21, 2017

(54) TILED DIGITAL RADIOGRAPHY DETECTORS FOR LONG-LENGTH IMAGING

(71) Applicant: Carestream Health, Inc., Rochester, NY (US)

(72) Inventors: Timothy J. Wojcik, Rochester, NY (US); Bradley S. Jadrich, Rochester, NY (US); Friedrich H. Üeffinger, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 78 days.

(21) Appl. No.: 14/942,081

(22) Filed: Nov. 16, 2015

(65) Prior Publication Data

US 2016/0135764 A1    May 19, 2016

Related U.S. Application Data

(60) Provisional application No. 62/080,454, filed on Nov. 17, 2014.

(51) Int. Cl.
*A61B 6/00* (2006.01)
(52) U.S. Cl.
CPC .......... *A61B 6/4233* (2013.01); *A61B 6/4283* (2013.01); *A61B 6/4411* (2013.01); *A61B 6/4405* (2013.01); *A61B 6/56* (2013.01)

(58) Field of Classification Search
CPC ....... A61B 6/4233; A61B 6/4283; G01T 1/16; G01T 1/2018; G01T 1/2012; G01T 1/2006; G01T 1/20; G01T 1/24
USPC .............. 378/189, 190; 250/586, 332, 208.2, 250/208.1, 581, 370.08
See application file for complete search history.

(56) References Cited

U.S. PATENT DOCUMENTS

| | | | |
|---|---|---|---|
| 5,440,130 A * | 8/1995 | Cox | G01T 1/2018 250/370.09 |
| 6,273,606 B1 | 8/2001 | Dewaele et al. | |
| 6,614,032 B2 | 9/2003 | Wendlandt | |
| 6,807,250 B2 | 10/2004 | Wang et al. | |
| 7,247,858 B2 | 7/2007 | De Keyser | |
| 7,498,583 B2 | 3/2009 | Shoji et al. | |
| 8,351,568 B2 | 1/2013 | Minnigh et al. | |
| 8,748,834 B2 | 6/2014 | Enomoto | |
| 2011/0233415 A1 | 9/2011 | Nakatsugawa et al. | |
| 2015/0131785 A1* | 5/2015 | Topfer | A61B 6/4233 378/98 |
| 2015/0247936 A1 | 9/2015 | Gemma et al. | |

FOREIGN PATENT DOCUMENTS

EP             0 919 856 B1    12/1997

* cited by examiner

*Primary Examiner* — Don Wong

(57) ABSTRACT

A digital radiographic detector having a radiolucent cover and housing at one or more edges of the detector allows radiographic imaging using multiple detector arrangements with overlapping edges that do not obstruct radiographic images captured thereby.

19 Claims, 12 Drawing Sheets

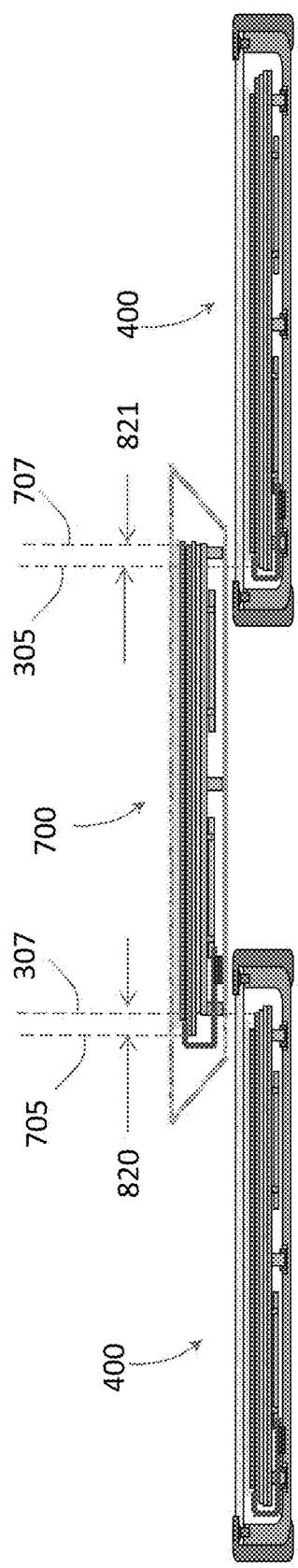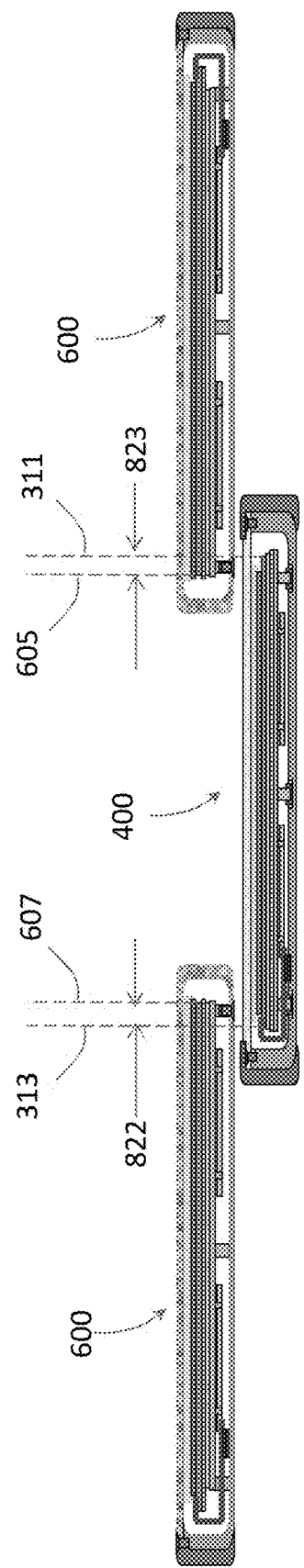
FIG. 8
FIG. 9

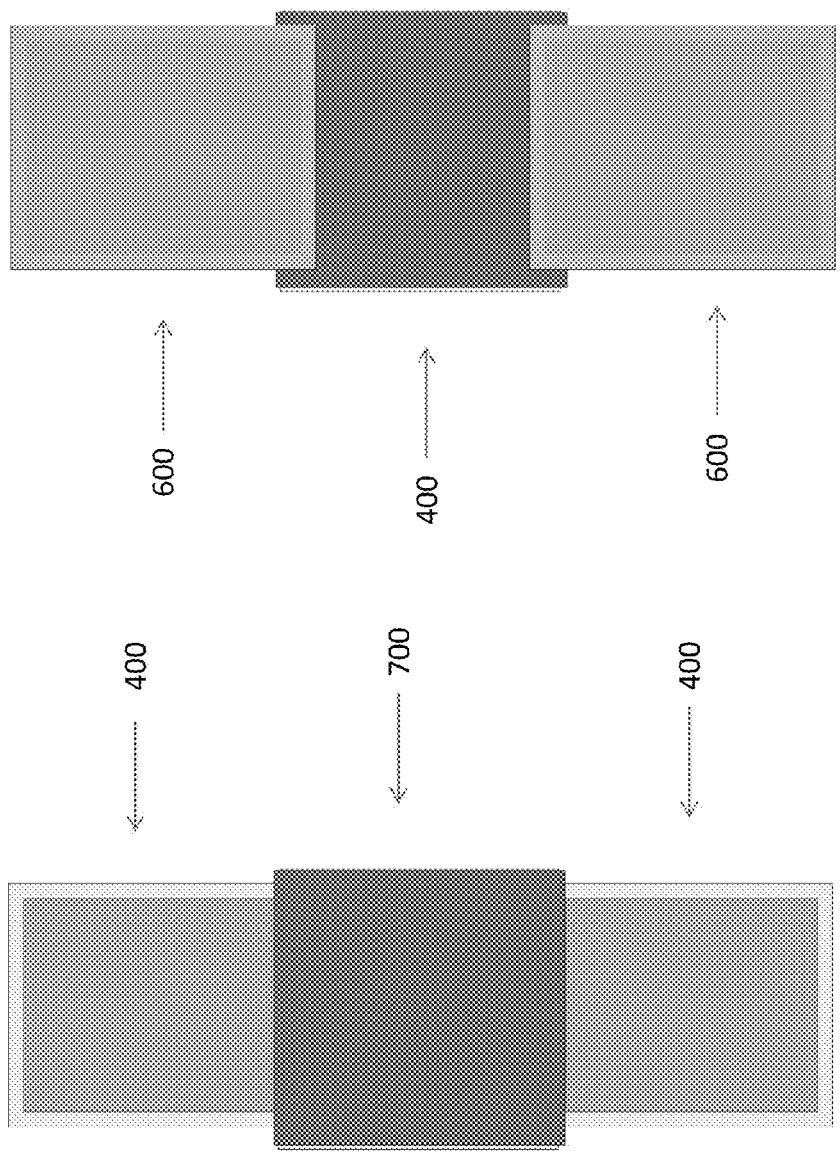

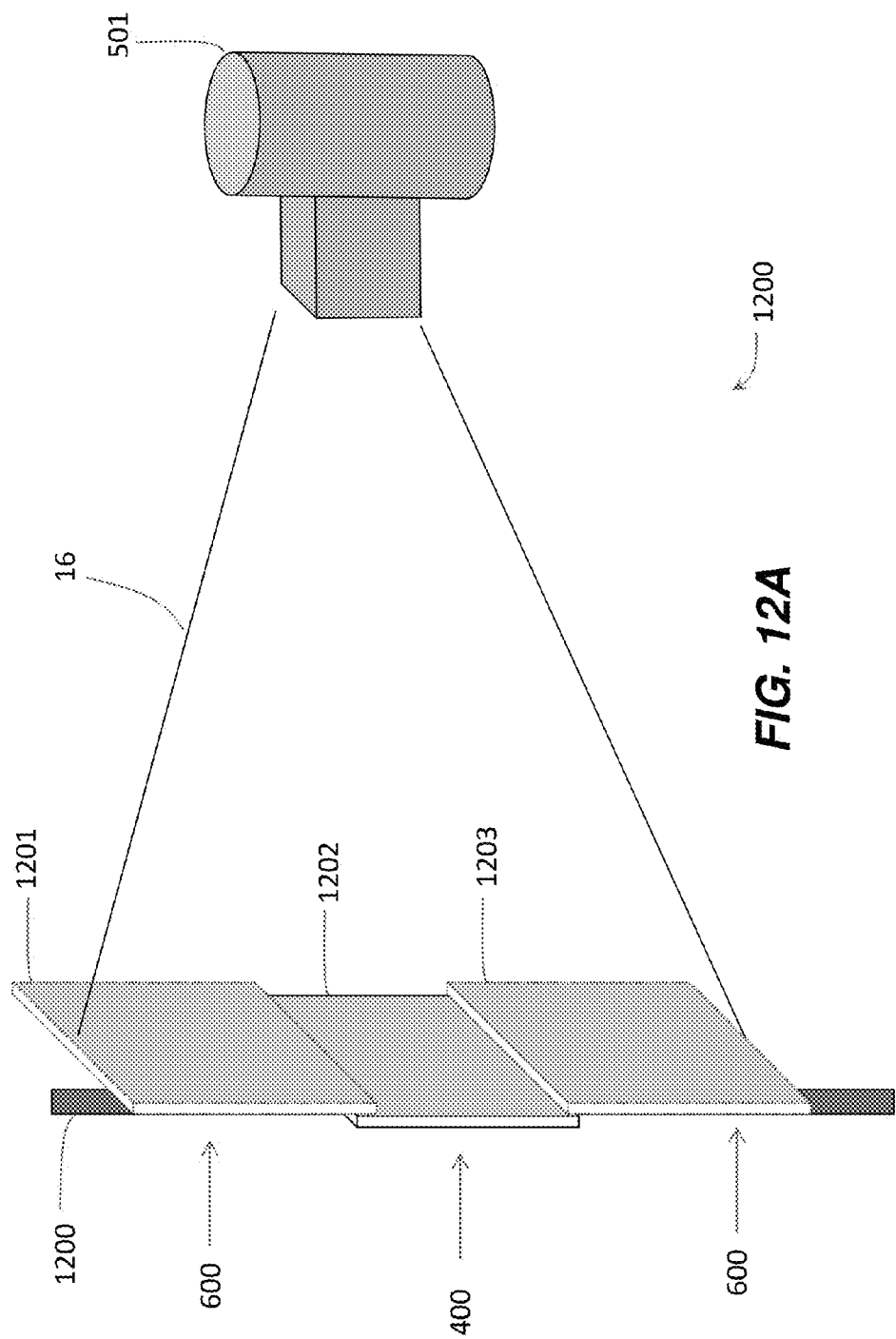

TILED DIGITAL RADIOGRAPHY DETECTORS FOR LONG-LENGTH IMAGING

CROSS REFERENCE TO RELATED APPLICATIONS

This application claims priority to U.S. Patent Application Ser. No. 62/080,454, filed Nov. 17, 2014, in the name of Wojcik et al., and entitled TILED DIGITAL RADIOGRAPHY DETECTORS FOR LONG-LENGTH IMAGING.

BACKGROUND OF THE INVENTION

The subject matter disclosed herein relates to digital radiography (DR) imaging, in particular, to long-length imaging that requires multiple DR detectors.

Special cassettes and films of extended length are sometimes used when imaging a long segment of a subject, such as a human body, with an analog screen-film technique. An x-ray source and the cassette are both centered to the subject to be examined and an x-ray collimator is adjusted to cover the imaging area, whereby a single x-ray exposure is performed. Flat-panel DR detectors are usually limited to 43 cm in length. For long-length imaging applications this would require separate exposures to be taken at different regions of the subject. In order to create a large, single composite image for diagnosis, the individually captured images of the subject need to be stitched together using digital computer-implemented reconstruction techniques.

Two primary approaches are available to acquire long-length imaging exams with flat-panel detectors. In both methods, the detector moves from one imaging position to the next behind the subject. In one known embodiment, the x-ray energy source moves (rotates or tilts) in order to track and expose the detector. In this x-ray source tilting method, the central x-ray pointing direction varies from one exposure position to the next to deliver the x-rays to the detector. In another known embodiment, the x-ray source focal spot position is not stationary, but translates synchronously with the DR detector parallel to the detector's axis of travel.

There are advantages to both embodiments. For example, the tilt method is free of parallax artifacts inherent in the x-ray source translation method. Because of parallax distortion, the geometric integrity of the subject's features in the stitched image may be degraded, particularly in the stitch overlap regions. Automatic image stitching can be achieved with high geometric accuracy such as provided by the Carestream DR DirectView Long-Length Imaging System. A high-precision hardware encoder reports the exact detector travel distance between exposures. In a direction transverse to the detector motion axis, software automatically analyzes the subject's features in the overlap regions to find the best alignment between any two adjacent images. The total stitch error has been demonstrated to be small under stringent exposure conditions.

Automatic exposure control can be used during the long-length imaging exams in order to apply just the right amount of exposure to each region of the subject for image quality. Software may also automatically adjust exposure discrepancies and compensate for the latitude differences, therefore providing optimized image presentation for each image. The image-processing reconstruction algorithm stitches together the individually optimized, display-presentation-ready images to create a smooth and seamless composite single image for diagnosis. The seam line between any two images may be blended without any visible artifacts during this digital process. Such imaging software should be able to adjust and fine-tune stitch positions to compensate for movement of the subject during the exam to avoid exposure retakes. In all of the examples just described, it would be advantageous if multiple DR detectors could be used to simultaneously capture a composite radiographic image of a subject in a single exposure.

The discussion above is merely provided for general background information and is not intended to be used as an aid in determining the scope of the claimed subject matter.

BRIEF DESCRIPTION OF THE INVENTION

A digital radiographic detector having a radiolucent cover and housing at one or more edges of the detector allows radiographic imaging using multiple detector arrangements with overlapping edges that do not obstruct radiographic images captured thereby. An advantage that may be realized in the practice of some disclosed embodiments of multiple DR detector systems is that the images are simultaneously exposed and potential movement of the subject during an imaging exam is eliminated, which results in improved long-length image reconstruction and reduced radiation exposure for a subject.

In one embodiment, a digital radiographic detector comprises a multilayer imaging structure with a substantially planar first side having a surface area defined by a plurality of edges. A rigid, radio-opaque housing portion substantially encloses the multilayer structure and surrounds one or more edges of the multilayer structure. A rigid, radiolucent housing portion is attached to the radio-opaque housing portion and surrounds one or more of the edges of the multilayer structure.

In another embodiment, a digital radiography detector comprises a multilayer structure. The multilayer structure includes a substantially planar first side having a surface area defined by a plurality of edges. An imaging device layer is used to receive light energy. A scintillator layer is adjacent the device layer and is used to convert radiographic energy to the light energy. A radiolucent layer covers the scintillator layer, and a rigid, radio-opaque housing substantially encloses the multilayer structure and surrounds one or more edges of the multilayer structure. A rigid, radiolucent housing surrounds one or more edges of the multilayer structure.

In another embodiment, a long-length imaging system comprises three or more digital radiographic detectors. A first detector comprises a multilayer structure with a substantially planar first side having a surface area defined by a plurality of edges. A device layer comprising a plurality of photosensors absorb light energy and a scintillator layer adjacent the device layer converts radiographic energy to the light energy. A radiolucent layer covers the scintillator layer and a rigid, radio-opaque housing substantially encloses the multilayer structure and surrounds one or more edges of the multilayer structure. A rigid, radiolucent housing surrounds one or more edges of the multilayer structure. Second and third detectors are disposed behind the first detector, in relation to a radiographic energy source aimed at the at least three detectors. Two of the edges of the first detectors overlap one edge of the second and third detectors.

In another embodiment, a long-length imaging system comprises three or more digital radiographic detectors. First and second detectors each comprise a multilayer structure with a substantially planar first side having a surface area defined by a plurality of edges. A device layer receives light energy, and a scintillator layer adjacent the device layer converts radiographic energy to the light energy. A radiolucent layer covers the scintillator layer, and a rigid, radio-opaque housing encloses the multilayer structure and surrounds one or more edges of the multilayer structure. A rigid, radiolucent housing portion surrounds one or more of the edges of the multilayer structure, and a third detector behind the first and second detectors, is overlapped by each of the first and second detectors.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. For example, the summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications. The drawings below are intended to be drawn neither to any precise scale with respect to relative size, angular relationship, relative position, or timing relationship, nor to any combinational relationship with respect to interchangeability, substitution, or representation of a required implementation. In the drawings, like numerals are used to indicate like parts throughout the various views. Thus, for further understanding of the invention, reference can be made to the following detailed description, read in connection with the drawings in which:

FIG. 8 is a cross-section of an exemplary arrangement of multiple DR detectors in a radiographic imaging system according to one embodiment;

FIG. 9 is a cross-section of an exemplary arrangement of multiple DR detectors in a radiographic imaging system according to one embodiment;

FIG. 10 is a top view of an exemplary arrangement of multiple DR detectors in a radiographic imaging system according to the embodiment of FIG. 8;

FIG. 11 is a top view of an exemplary arrangement of multiple DR detectors in a radiographic imaging system according to the embodiment of FIG. 9;

FIG. 12A is a perspective view of an imaging system implementing an arrangement of DR detectors according to one embodiment;

DETAILED DESCRIPTION OF THE INVENTION

Figure 1:
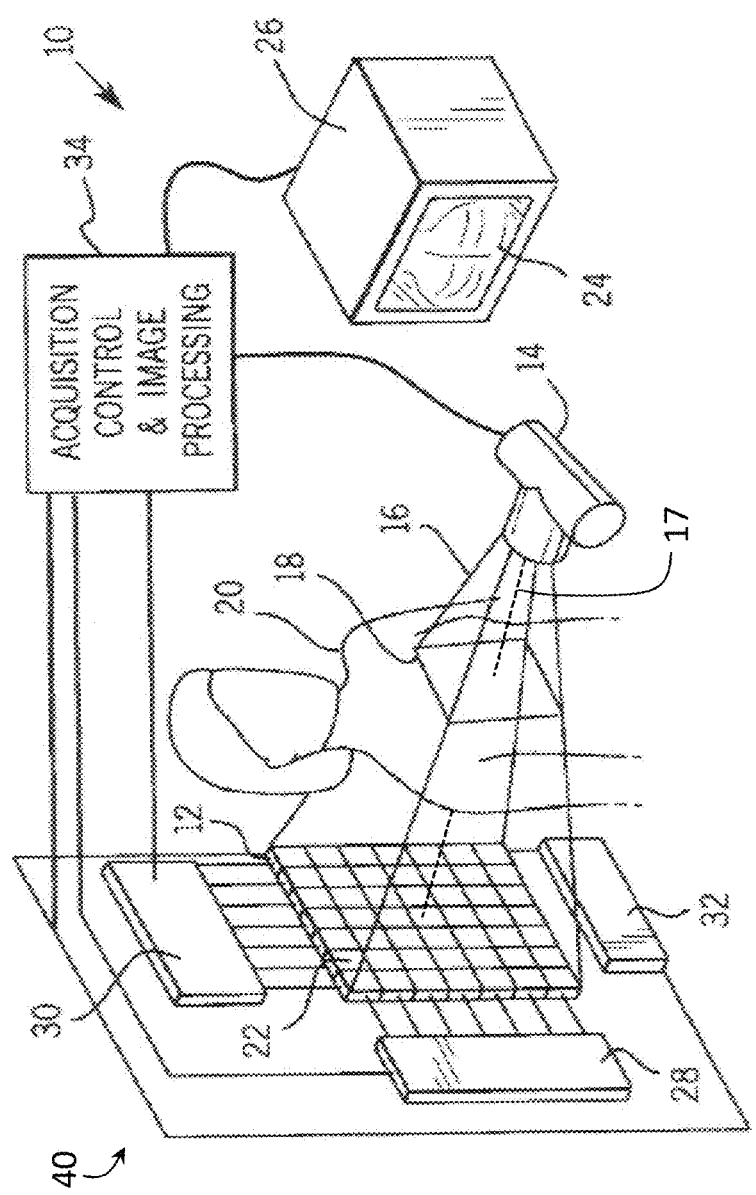
FIG. 1 is a diagram of an exemplary radiographic imaging system.

FIG. 1 is a perspective view of a digital radiographic (DR) imaging system 10 that includes a generally planar DR detector 40 (shown without a housing for clarity of description), an x-ray source 14 configured to generate radiographic energy (x-ray radiation), and a digital monitor 26 configured to display images captured by the DR detector 40, according to one embodiment. The DR detector 40 may include a two dimensional array 12 of detector cells 22 (photosensors), arranged in electronically addressable rows and columns. The DR detector 40 may be positioned to receive x-rays 16 passing through a subject 20 during a radiographic energy exposure, or radiographic energy pulse, emitted by the x-ray source 14. As shown in FIG. 1, the radiographic imaging system 10 may use an x-ray source 14 that emits collimated x-rays 16, e.g. an x-ray beam, selectively aimed at and passing through a preselected region 18 of the subject 20. The x-ray beam 16 may be attenuated by varying degrees along its plurality of rays according to the internal structure of the subject 20, which attenuated rays are detected by the array 12 of photosensitive detector cells 22. The planar DR detector 40 is positioned, as much as possible, in a perpendicular relation to a substantially central ray 17 of the plurality of rays 16 emitted by the x-ray source 14. The array 12 of individual photosensitive cells (pixels) 22 may be electronically addressed (scanned) by their position according to column and row. As used herein, the terms "column" and "row" refer to the vertical and horizontal arrangement of the photo sensor cells 22 and, for clarity of description, it will be assumed that the rows extend horizontally and the columns extend vertically. However, the orientation of the columns and rows is arbitrary and does not limit the scope of any embodiments disclosed herein. Furthermore, the term "subject" may be illustrated as a human patient in the description of FIG. 1, however, a subject of a DR imaging system, as the term is used herein, may be a human, an animal, an inanimate object, or a portion thereof.

In one exemplary embodiment, the rows of photosensitive cells 22 may be scanned one or more at a time by electronic scanning circuit 28 so that the exposure data from the array 12 may be transmitted to electronic read-out circuit 30. Each photosensitive cell 22 may independently store a charge proportional to an intensity, or energy level, of the attenuated radiographic radiation, or x-rays, received and absorbed in the cell. Thus, each photosensitive cell, when read-out, provides information defining a pixel of a radiographic image 24, e.g. a brightness level or an amount of energy absorbed by the pixel, that may be digitally decoded by image processing electronics 34 and transmitted to be displayed by the digital monitor 26 for viewing by a user. An electronic bias circuit 32 is electrically connected to the two-dimensional detector array 12 to provide a bias voltage to each of the photosensitive cells 22.

Each of the bias circuit 32, the scanning circuit 28, and the read-out circuit 30, may communicate with an acquisition control and image processing unit 34 over a connected cable 33 (wired) or over a wireless transmitter 35. The DR detector may be equipped to transmit radiographic image data, and to exchange control and other signals, such as preparatory ready signals, over the cable 33 or wirelessly over transmitter 35 with the acquisition control and image processing unit 34, which may also include an image processing computer system. The acquisition control and image processing unit 34 may include a processor and electronic memory (not shown) to control operations of the DR detector 40 as described herein, including control of circuits 28, 30, and 32, for example, by use of programmed instructions. The acquisition control and image processing unit 34 may also be used to control activation of the x-ray source 14 during a radiographic exposure, controlling an x-ray tube electric current magnitude, and thus the fluence of x-rays in x-ray beam 16, and/or the x-ray tube voltage, and thus the energy level of the x-rays in x-ray beam 16.

The acquisition control and image processing unit 34 may transmit image (pixel) data to the monitor 26, based on the radiographic exposure data received from the array 12 of photosensitive cells 22. Alternatively, acquisition control and image processing unit 34 can process the image data and store it, or it may store raw unprocessed image data, in local or remotely accessible memory.

With regard to a direct detection embodiment of DR detector 40, the photosensitive cells 22 may each include a sensing element sensitive to x-rays, i.e. it absorbs x-rays and generates an amount of charge carriers in proportion to a magnitude of the absorbed x-ray energy. A switching element may be configured to be selectively activated to read out the charge level of a corresponding x-ray sensing element. With regard to an indirect detection embodiment of DR detector 40, photosensitive cells 22 may each include a sensing element sensitive to light rays in the visible spectrum, i.e. it absorbs light rays and generates an amount of charge carriers in proportion to a magnitude of the absorbed light energy, and a switching element that is selectively activated to read the charge level of the corresponding sensing element. A scintillator, or wavelength converter, is disposed over the light sensitive sensing elements to convert incident x-ray radiographic energy to visible light energy. Thus, in the embodiments disclosed herein, it should be noted that the DR detector 40 (or DR detector 300 in FIG. 3 or DR detector 400 in FIG. 4) may include an indirect or direct type of DR detector.

Examples of sensing elements used in sensing array 12 include various types of photoelectric conversion devices (e.g., photosensors) such as photodiodes (P-N or PIN diodes), photo-capacitors (MIS), photo-transistors or photoconductors. Examples of switching elements used for signal read-out include MOS transistors, bipolar transistors and other p-n junction components.

Figure 2:
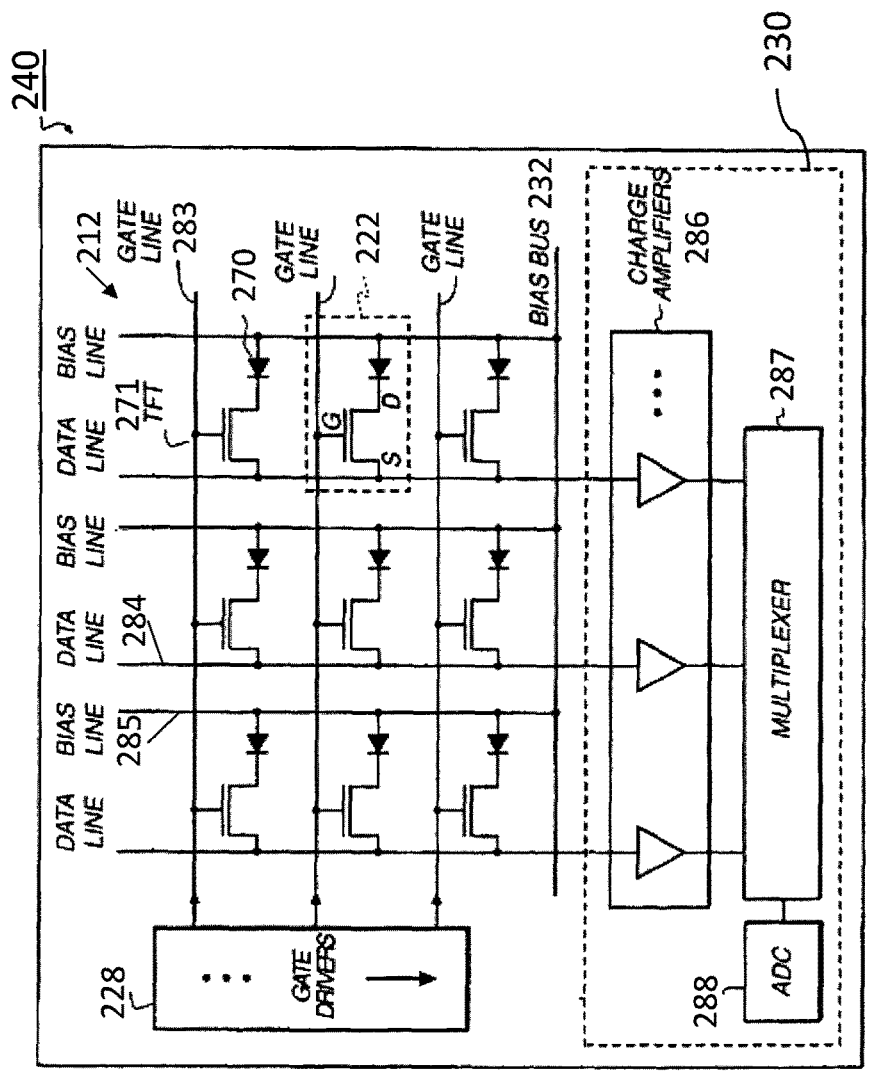
FIG. 2 is a schematic diagram of an imaging array for an exemplary radiographic detector.

FIG. 2 is a schematic diagram 240 of a portion of a two-dimensional array 12 for a DR detector 40. The array of photosensor cells 212, whose operation may be consistent with the photosensor array 12 described above, may include a number of hydrogenated amorphous silicon (a-Si:H) n-i-p photodiodes 270 and thin film transistors (TFTs) 271 formed as field effect transistors (FETs) each having gate (G), source (S), and drain (D) terminals. In embodiments of DR detector 40 disclosed herein, such as a multilayer DR detector (400 of FIG. 4), the two-dimensional array of photosensor cells 12 may be formed in a device layer that abuts adjacent layers of the DR detector structure. A plurality of gate driver circuits 228 may be electrically connected to a plurality of gate lines 283 which control a voltage applied to the gates of TFTs 271, a plurality of readout circuits 230 may be electrically connected to data lines 284, and a plurality of bias lines 285 may be electrically connected to a bias line bus or a variable bias reference voltage line 232 which controls a voltage applied to the photodiodes 270. Charge amplifiers 286 may be electrically connected to the data lines 284 to receive signals therefrom. Outputs from the charge amplifiers 286 may be electrically connected to a multiplexer 287, such as an analog multiplexer, then to an analog-to-digital converter (ADC) 288, or they may be directly connected to the ADC, to stream out the digital radiographic image data at desired rates. In one embodiment, the schematic diagram of FIG. 2 may represent a portion of a DR detector 40 such as an a-Si:H based indirect flat panel imager as described below with respect to the exemplary embodiments of FIGS. 4, 6, and 7.

Incident x-rays, or x-ray photons, 16 are converted to optical photons, or light rays, by a scintillator, which light rays are subsequently converted to electron-hole pairs, or charges, upon impacting the a-Si:H n-i-p photodiodes 270. In one embodiment, an exemplary detector cell 222, which may be equivalently referred to herein as a pixel, may include a photodiode 270 having its anode electrically connected to a bias line 285 and its cathode electrically connected to the drain (D) of TFT 271. The bias reference voltage line 232 can control a bias voltage of the photodiodes 270 at each of the detector cells 222. The charge capacity of each of the photodiodes 270 is a function of its bias voltage and its capacitance. In general, a reverse bias voltage, e.g. a negative voltage, may be applied to the bias lines 285 to create an electric field (and hence a depletion region) across the pn junction of each of the photodiodes 270 to enhance its collection efficiency for the charges generated by incident light rays. The image signal represented by the array of photosensor cells 212 may be integrated by the photodiodes while their associated TFTs 271 are held in a non-conducting (off) state, for example, by maintaining the gate lines 283 at a negative voltage via the gate driver circuits 228. The photosensor cell array 212 may be read out by sequentially switching rows of the TFTs 271 to a conducting (on) state by means of the gate driver circuits 228. When a row of the pixels 22 is switched to a conducting state, for example by applying a positive voltage to the corresponding gate line 283, collected charge from the photodiode in those pixels may be transferred along data lines 284 and integrated by the external charge amplifier circuits 286. The row may then be switched back to a non-conducting state, and the process is repeated for each row until the entire array of photosensor cells 212 has been read out. The integrated signal outputs are transferred from the external charge amplifiers 286 to an analog-to-digital converter (ADC) 288 using a parallel-to-serial converter, such as multiplexer 287, which together comprise read-out circuit 230.

This digital image information may be subsequently processed by image processing system 34 to yield a digital image which may then be digitally stored and immediately displayed on monitor 26, or it may be displayed at a later time by accessing the digital electronic memory containing the stored image. The flat panel DR detector 40 having an imaging array as described with reference to FIG. 2 is capable of both single-shot (e.g., static, radiographic) and continuous (e.g., fluoroscopic) image acquisition.

Figure 3:
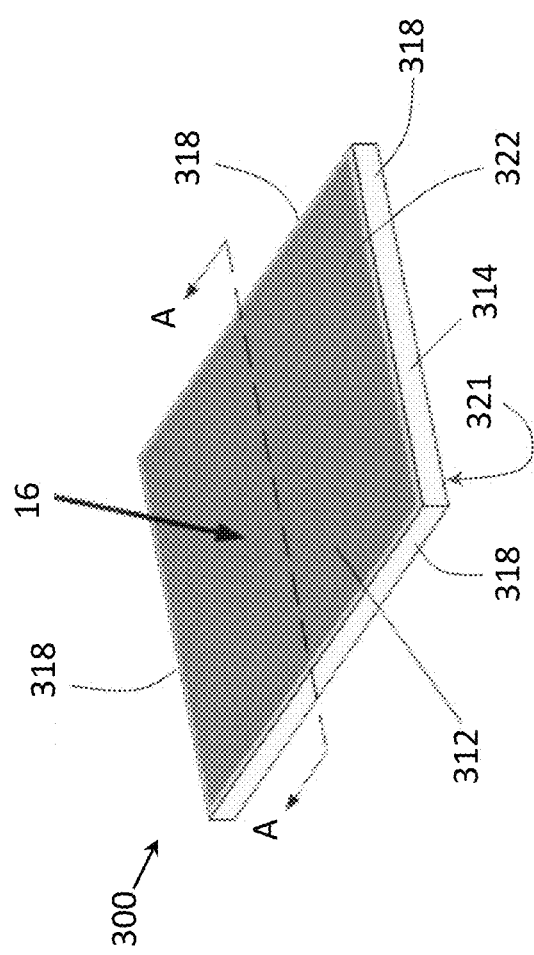
FIG. 3 shows a perspective view of an exemplary portable wireless DR detector.

FIG. 3 shows a perspective view of an exemplary prior art generally rectangular, planar, portable wireless DR detector 300 according to an embodiment of DR detector 40 disclosed herein. The DR detector 300 may include a housing portion 314 that surrounds a multilayer structure comprising the photosensor array portion 22 of the DR detector 300. The housing portion 314 of the DR detector 300 may include a continuous, rigid, x-ray opaque material or, as used synonymously herein a radio-opaque material, surrounding an interior volume of the DR detector 300. The housing portion 314 comprises four edges 318, extending between the top side 321 and the bottom side 322, and arranged substantially orthogonally in relation to the top and bottom sides 321, 322. The bottom side 322 may be continuous with the four edges and disposed opposite the top side 321 of the DR detector 300. The top side 321 comprises a top cover 312 attached to the housing portion 314 which, together with the housing portion 314, substantially encloses the multilayer structure in the interior volume of the DR detector 300. The top cover 312 may be attached to the housing 314 to form a seal therebetween, and be made of a material that passes x-rays 16 without significant attenuation thereof, i.e., an x-ray transmissive material or, as used synonymously herein, a radiolucent material, such as carbon fiber and plastic, polymeric, or other plastic based material.

Figure 4:
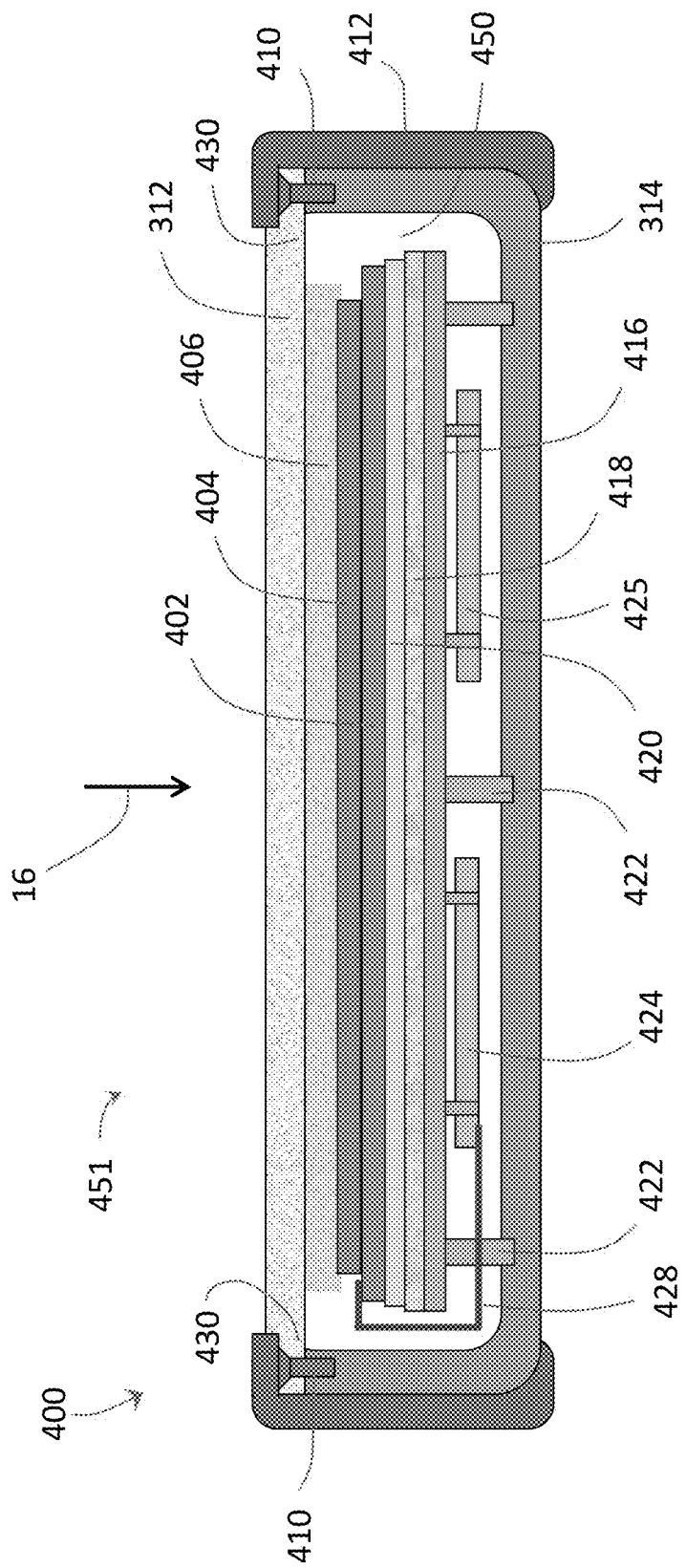
FIG. 4 is a cross-section of a portion of the exemplary portable wireless DR detector of FIG. 3 along section line A-A.

With reference to FIG. 4, there is illustrated in schematic form an exemplary cross-section view along section A-A of the exemplary embodiment of the DR detector 300 (FIG. 3). For spatial reference purposes, one major surface of the DR detector 400 may be referred to as the top side 451 and a second major surface may be referred to as the bottom side 452, as used herein. The embodiment of the DR detector 400 depicted in FIG. 4 may be referred to herein as a "standard" DR detector. The multilayer structure is disposed within the interior volume 450 enclosed by the housing 314 and top cover 312 and may include a substantially planar scintillator layer 404 over the two-dimensional imaging sensor array 12 shown schematically as the device layer 402. The scintillator layer 404 may be directly under (e.g., directly connected to) the substantially planar top cover 312, and the imaging array 402 may be directly under the scintillator 404. Alternatively, a flexible layer 406 may be positioned between the scintillator layer 404 and the top cover 312 as part of the multilayer structure to provide shock absorption. The flexible layer 406 may be selected to provide an amount of flexible support for both the top cover 312 and the scintillator 404, and may comprise a foam rubber type of material. The layers just described comprising the multilayer structure each may generally be formed in a rectangular shape and defined by edges arranged orthogonally and disposed in parallel with an interior side of the edges 318 of the housing 314, as described in reference to FIG. 3.

A substrate layer 420 may be disposed under the imaging array 402, such as a rigid glass layer upon which the array of photosensors 402 is formed, and may comprise another layer of the multilayer structure. Under the substrate layer 420 a radio-opaque shield layer 418 may be used as an x-ray blocking layer to help prevent scattering of x-rays passing through the substrate layer 420 as well as to block x-rays reflected from other surfaces in the interior volume 450. Readout electronics, including the scanning circuit 28, the read-out circuit 30, and the bias circuit 32 (all of FIG. 1) may be formed co-planar with the imaging array 402 or, as shown, may be disposed below frame support member 416 in the form of integrated circuits electrically connected to printed circuit boards 424. The frame support member 416 is fixed to the housing 314 using frame support beams 422 to provide support for the multilayer structure just described. The imaging array 402 is electrically connected to the integrated circuit readout electronics 424 over a flexible connector 428 which may comprise a plurality of flexible, sealed conductors. X-ray flux may pass through the radiolucent top panel cover 312, in the direction represented by an exemplary x-ray beam 16, and impinge upon scintillator 404 where stimulation by the high-energy x-rays 16, or photons, causes the scintillator 404 to emit lower energy photons as visible light rays which are then received in the photosensors of imaging array 402. The frame support member 416 may securely mount the multilayer structure to the housing 314 and may further operate as a shock absorber by disposing elastic pads (not shown) between the frame support beams 422 and the housing 314. Fasteners 410, such as screws, may be used to fixedly attach the top cover 312 to the housing 314 and create a seal therebetween in the region 430 where they come into contact. In one embodiment, an external bumper 412 may be attached along the edges 318 of the DR detector 400 to provide additional shock-absorption.

Figure 5:
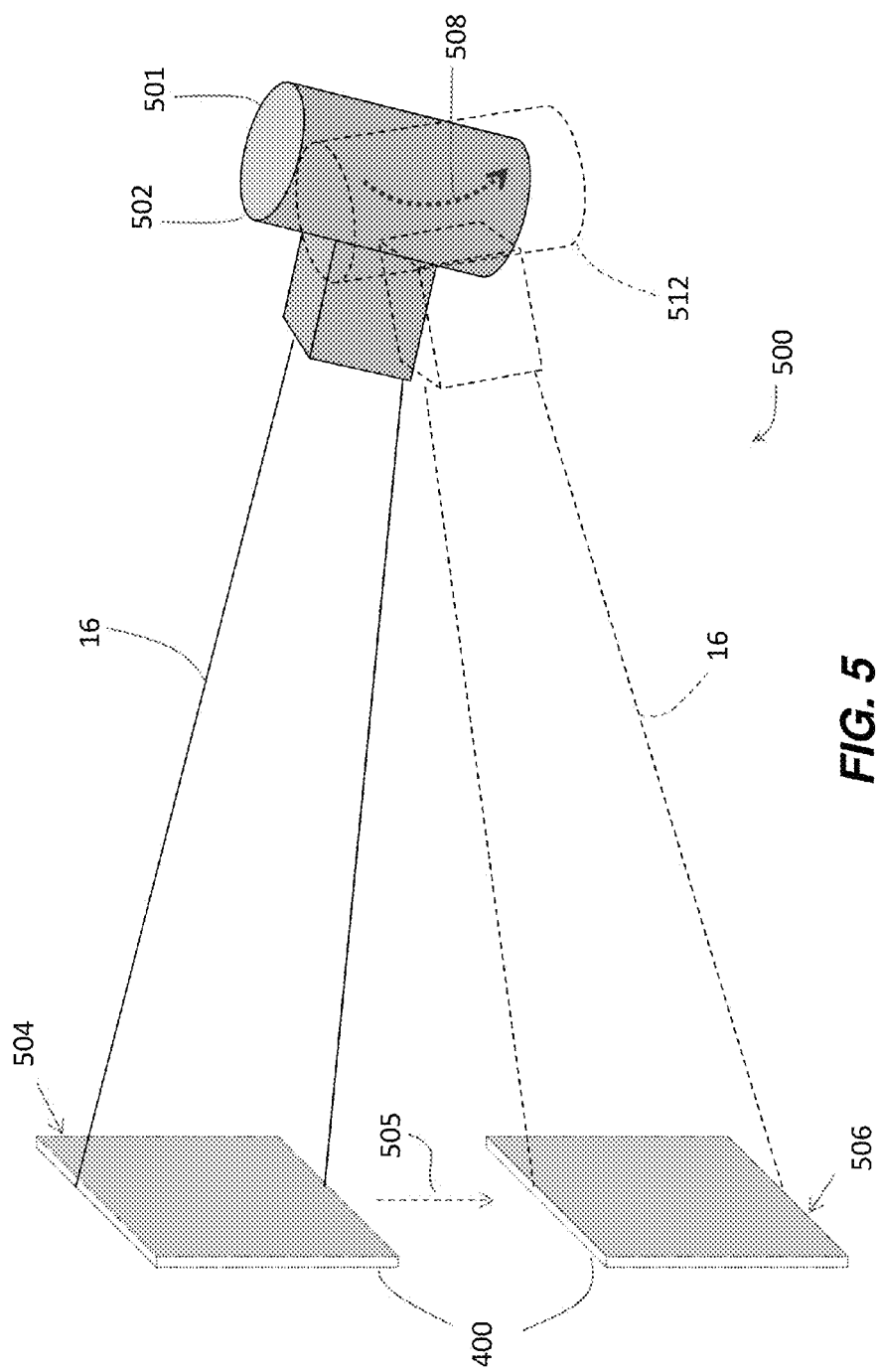
FIG. 5 is a diagram of an exemplary radiographic imaging system illustrating positioning of the radiographic energy source and the DR detector.

FIG. 5 illustrates operation of an embodiment of an imaging system 500 which may be used for long-length radiographic imaging of a stationary subject (not shown) positioned between an x-ray source 501 and DR detector 400. The x-ray radiation source 501 in the first position 502 is aimed at DR detector 400 in position 504 to capture a first radiographic image of the subject. In the embodiment shown in FIG. 5, the x-ray radiation source may be tilted in the direction indicated by arrow 508 to a second position 512 and aimed at DR detector 400 in position 506 to capture a second image of the stationary subject, wherein the first and second images each include an image of a different region of the same subject. In the embodiment of FIG. 5, a single DR detector 400 may be moved in the direction indicated by arrow 505 from the first position 504 to the second position 506 to capture the two images of the subject as just described. In another embodiment, two separate DR detectors 400 may be used, one in each of positions 504 and 506, wherein each DR detector 400 is exposed to one radiographic pulse from the x-ray source 501 firing first and second radiographic energy pulses at positions 502 and 512. In another embodiment, the DR detector 400 may be moved to one or more intermediate positions between positions 504 and 506, with corresponding intermediate tilt positions of the x-ray source 501 between positions 502 and 512 to capture one or more additional radiographic images. In another embodiment, the x-ray source may be attached to a support at a fixed angle such that the x-ray source 501 is not tiltable, rather, the support is configured to move vertically and is used to translate the x-ray source 501 to a position corresponding to the DR detector positions 504 and 506, or to the intermediate positions of the DR detector 400 as just described. Thus, it should be understood that embodiments of imaging system 500 may include various combinations of one or more DR detectors 400, which may be fixed or moveable, together with an x-ray source 501 that may be tiltable and/or vertically translatable. In one embodiment, the one or more positions of DR detector 400 may overlap, resulting in a plurality of captured radiographic images that may be stitched together into one long-length digital image of the subject using known computer-implemented image reconstruction processing techniques.

Figure 6:
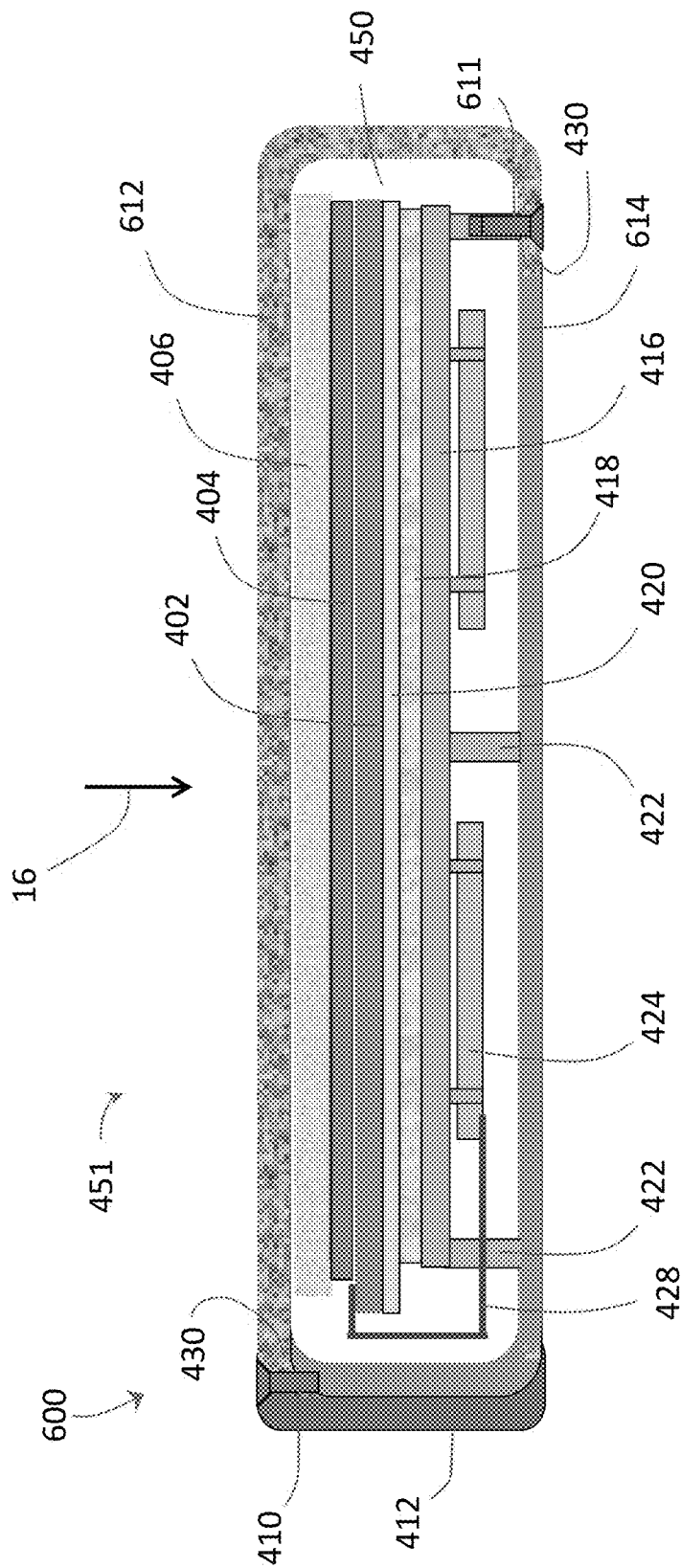
FIG. 6 is a cross-section of a portion of an exemplary portable wireless DR detector according to one embodiment.

FIG. 6 illustrates in schematic form another exemplary cross-section view along section A-A of the exemplary embodiment of the DR detector 300 (FIG. 3). Several of the components in the DR detector 600 illustrated in FIG. 6 are similar in most respects to the components as described with respect to the DR detector 400 of FIG. 4 and are identified with the same element numerals. The description of those components bearing the same element numerals is not repeated here. The DR detector 600 comprises a housing 614 having a portion made from a radio-opaque material extending along a bottom portion of the DR detector 600 and also continuously forms at least one edge of the housing 614 which, in the perspective of FIG. 6, is located to the left of the interior volume 450. In separate embodiments, the radio-opaque portion of the housing 614 may continuously extend long one, two, or three edges of a DR detector 600 having four edges. If the radio-opaque portion of the housing 614 extends along two edges, it may extend along any two adjacent and substantially perpendicular edges or along any pair of opposite substantially parallel edges of the DR detector 600.

In the exemplary embodiment of FIG. 6, a portion of the housing 612 is formed from a radiolucent material. This portion of the housing may comprise a continuous extension of the top cover 312 (FIG. 4) to form a portion of the housing 612 for the DR detector 600 that is transparent to x-ray radiation. In separate embodiments, the radiolucent portion of the housing 612 may continuously extend along one, two, or three edges of a DR detector 600 having four edges. If the radiolucent portion of the housing 612 extends along two edges, it may extend along any two adjacent substantially perpendicular edges or along any pair of opposite substantially parallel edges of the DR detector 600. In order to fasten the radiolucent portion of the housing 612, a fastener 611, similar in material and shape as fastener 410, may be used in the bottom side of the DR detector to sealingly fasten the radiolucent edge of the housing 612 to the frame support 416 or to a frame support beam 422. At the edges of the DR detector 600 where the radio-opaque housing 614 extends along the edges toward the top side 451, the fastener 410 may used as described herein to sealingly fasten it to the radiolucent portion of the housing 612. The fastener 611 is positioned in the bottom side 452 to minimize or eliminate placement of any DR detector components that are not radiolucent above, or beyond an edge of, the imaging layer 402 closest to a radiolucent edge of the DR detector 600. This helps to prevent artifacts appearing on radiographic images captured using multiple overlapping DR detectors 600 as described hereinbelow. Similarly, the integrated circuit readout electronics 424 are positioned proximate a (bottom) side of the sensor array imaging device layer 402 that is opposite the x-ray source to minimize or eliminate placement of any electronic components that are not radiolucent above, or beyond an edge of, the imaging device layer 402 closest to a radiolucent edge of the DR detector 600.

Figure 7:
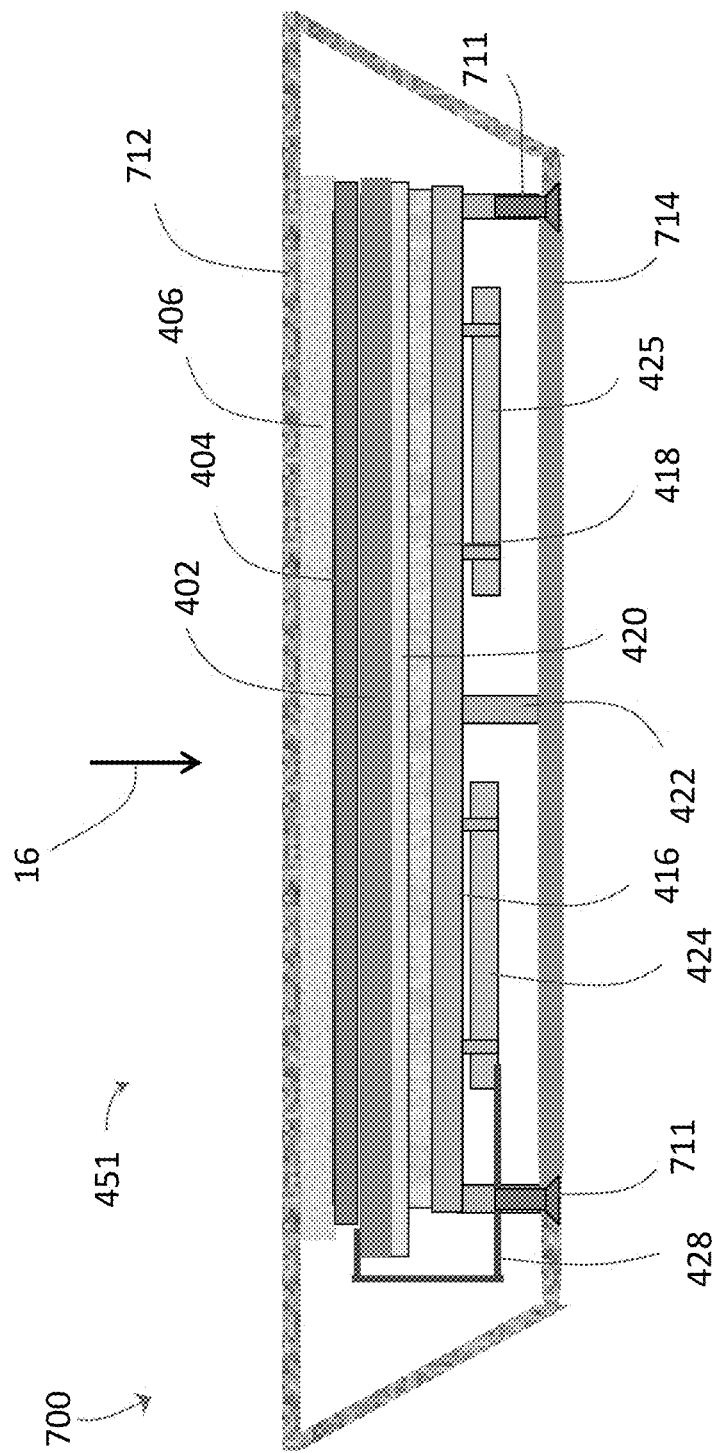
FIG. 7 is a cross-section of a portion of an exemplary portable wireless DR detector according to one embodiment.

FIG. 7 illustrates in schematic form another exemplary cross-section view along section A-A of the exemplary embodiment of the DR detector 300 (FIG. 3). Several of the components in the DR detector 700 illustrated in FIG. 7, such as the multilayer structure, are similar in most respects to the components as described with respect to the DR detector 400 of FIG. 4 and are identified with the same element numerals. The description of those components bearing the same element numerals is not repeated here. The DR detector 700 comprises a housing having a portion made from a radio-opaque material 714 extending along a bottom portion of the DR detector 700 and may continuously form one or two edges of the housing 714 wherein, in the perspective of FIG. 7, one such edge may be located behind the multilayer structure as depicted therein. In separate embodiments, the radio-opaque portion of the housing 714 may continuously extend long one or two edges of the housing 712 of the DR detector 700 having four edges. If the radio-opaque portion of the housing 714 extends along two edges, it may extend along opposite edges of the DR detector 700.

In the exemplary embodiment of FIG. 7, a portion of the housing 712 is formed from a radiolucent material. This portion of the housing may comprise a continuous extension of the top cover 312 (FIG. 4) to form opposite edges of the housing 712 for the DR detector 700 that are transparent to x-ray radiation. In separate embodiments, the radiolucent portion of the housing 712 may continuously extend along two, three, or all edges of a DR detector 700 having four edges. In the perspective of FIG. 7, two opposite edges (left and right) are formed from a radiolucent material, such as a carbon fiber reinforced plastic, polymeric, or other plastic based material. The housing 712 may extend vertically between the top side and the bottom side, or it may extend at a non-orthogonal angle therebetween, as shown in FIG. 7. In order to fasten the radiolucent portion of the housing 712, fasteners 711, similar in material and shape as fastener 410, may be used in the bottom side of the DR detector to sealingly fasten the radiolucent edge of the housing 712 to the frame support 416, or to the frame support beam 422, as shown. The fasteners 711, as well as integrated circuit readout electronics 424 are positioned proximate the bottom side 452, which is a side of the sensor array imaging device layer 402 that is opposite the x-ray source to minimize or eliminate placement of any DR detector components that are not radiolucent above, or beyond an edge of, the imaging layer 402 closest to a radiolucent edge of the DR detector 600. This helps to prevent artifacts appearing on radiographic images captured using multiple overlapping DR detectors 700 as described hereinbelow.

As described herein, DR detector embodiments 400, 600, and 700 are usable individually, as in standard diagnostic radiographic imaging practice, and may be combined, or tiled, as described herein, for long-length imaging. FIG. 8 illustrates a side view of an exemplary arrangement of three DR detectors including two standard DR detectors 400, and a central DR detector 700, as describe herein with reference to FIG. 7, having at least two opposite edges of its housing formed from radiolucent material that each overlap one edge of one of the standard DR detectors 400, as shown. The central DR detector 700 is positioned forward of the standard DR detectors 400 in relation to an x-ray energy source positioned to emit x-rays in a direction as depicted in FIG. 4 and FIG. 7. The central DR detector includes an imaging array layer having one of its edges 705 overlapping an edge of the imaging array layer 307, in a corresponding first one of the standard DR detectors 400, by a distance 820, and an opposite edge of the imaging array layer 707 overlapping an edge of the imaging array 305, in a corresponding second one of the standard DR detectors 400, by a distance 821. The overlapping distances 820, 821 may be equivalent or different. The overlap distance is not critical to the presently disclosed invention, and may range from one or more millimeters to tens or hundreds of millimeters. Because the edges of the DR detector 700 that overlap the edges of the standard DR detectors 400 are radiolucent, and have eliminated or minimized components, such as electronic readout circuits, beyond the edges of the imaging layer 402 therein, a radiographic image captured simultaneously by the three detectors as depicted in FIG. 8, will not include unnecessary artifacts in the portions of the radiographic image captured by the standard DR detectors 400 caused by radio-opaque components in the central DR detector 700 that otherwise would be disposed therein beyond the overlapping region if DR detector 700 was configured as a standard DR detector. One advantage of the embodiment depicted in FIG. 8 is that the two prior art standard detectors 400 may be used to capture a long-length image when combined as shown with only one new modified DR detector 700. The embodiment illustrated in FIG. 8 does not require obtaining several DR detectors with modified radiolucent edges. Thus, a radiographic image simultaneously captured by the three DR detectors arranged as in FIG. 8, may be accurately stitched together, without having to mask or process unnecessary artifacts, using standard computer implemented digital reconstruction techniques. Such known digital reconstruction methods include techniques for correcting geometric alignment of images from DR detectors having different source-to-image distance. In the example embodiment shown in FIG. 8, a source-to-image distance of the DR detector 700 may be less than that of the DR detectors 400.

FIG. 9 illustrates a side view of an exemplary arrangement of DR detectors including one standard central DR detector 400, and two DR detectors 600, as described herein with reference to FIG. 6, each having one edge of its housing formed from radiolucent material that overlaps one edge of the standard central DR detector 400, as shown. The central standard DR detector 400 is positioned rearward of the DR detectors 600 in relation to an x-ray energy source positioned to emit x-rays in a direction as depicted in FIG. 4 and FIG. 6. The central standard DR detector 400 includes an imaging array layer having one of its edges 313 overlapped by an edge of the imaging array layer 607 in a corresponding first one of the DR detectors 600 by a distance 822, and an opposite edge of the imaging array layer 311 overlapped by an edge of the imaging array layer 605 by a distance 823 in a corresponding second one of the DR detectors 600. The overlapping distances 822, 823 may be equivalent or different. The overlap distance is not critical to the presently disclosed invention, and may range from one or more millimeters to tens or hundreds of millimeters. Because the respective edge of each of the DR detectors 600 that overlaps the edge of the standard DR detector 400 is radiolucent, and has eliminated or minimized radio-opaque components, such as integrated electronic read out circuits, beyond the edge of the imaging layer therein, a radiographic image captured simultaneously by the three detectors as depicted in FIG. 9, will not include unnecessary artifacts in the portion of the radiographic image as captured by the standard DR detector 400 caused by radio-opaque components in the DR detectors 600 that otherwise would be disposed therein beyond the overlapping region if DR detectors 600 were configured as standard DR detectors. One advantage of the embodiment depicted in FIG. 9 is that a prior art standard detector 400 may be used to capture a long-length image when combined as shown with two new modified DR detectors 600 each having only one edge modified to be radiolucent. The embodiment illustrated in FIG. 8 does not require obtaining several DR detectors with modified radiolucent edges. Thus, a radiographic image simultaneously captured by the three DR detectors arranged as in FIG. 9, may be accurately stitched together without having to mask or process unnecessary artifacts using standard computer implemented digital reconstruction techniques. Such known digital reconstruction methods include techniques for correcting geometric alignment of images from DR detectors having different source-to-image distance. In the example embodiment shown in FIG. 9, a source-to-image distance of the DR detectors 600 may be less than that of the DR detector 400.

FIGS. 10 and 11 illustrate top views of the DR detector arrangements as depicted in FIGS. 8 and 9, respectively. As shown, two standard DR detectors 400 are positioned rearward of the DR detector 700 in FIG. 10, in relation to an x-ray source that, in the perspective of FIG. 10, emits x-ray energy into the page. The DR detector 700 includes radiolucent edges at its top and bottom edges in the Figure, which overlap the edges of the DR detectors 400, as described in relation to FIG. 8. In FIG. 11, two DR detectors 600, each as described and configured in the description of FIG. 6, are positioned forward of the standard DR detectors 400 in FIG. 11, in relation to an x-ray source that, in the perspective of FIG. 11, emits x-ray energy into the page. The DR detectors 600 each include at least one radiolucent edge (top or bottom edge) which overlaps a corresponding edge of the standard DR detector 400, as described in relation to FIG. 9. While particular arrangements of DR detectors have been illustrated in FIGS. 8-11, it should be noted that those skilled in the art may envisage that various combinations of DR detectors may be implemented in various geometric combinations. Thus, different types of DR detectors may be utilized in upper, central, or lower positions, or may be used in combination with four or more detectors, having edges overlapping, wherein each of the DR detectors may be configured to include one, two, three, or four radiolucent edges. Such combinations are considered to be within the scope of the present invention so long as any radio-opaque edges of a DR detector do not interfere with the x-ray beams incident upon an imaging array of another DR detector. Such radio-opaque edges may be positioned rearward of another overlapping DR detector, or may be positioned on an exterior border of the arrangement of DR detectors. Alternatively, some or all of the tiled DR detectors may be arranged in a staggered stepwise fashion (FIG. 13), rather than having one central DR detector positioned forward or rearward of the other detectors.

Figure 12B:
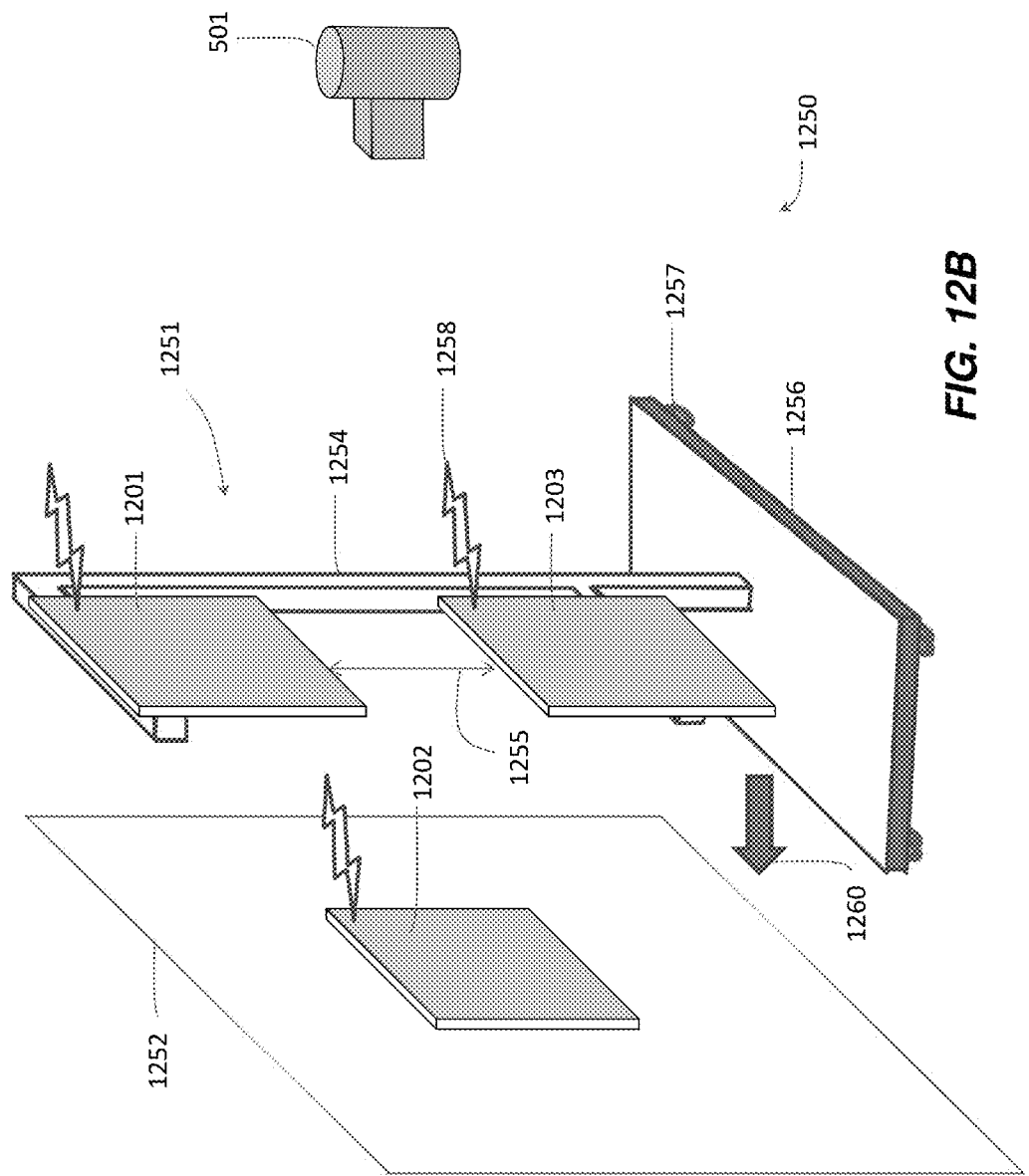
FIG. 12B is a perspective view of an imaging system implementing an arrangement of DR detectors according to one embodiment.

FIG. 12A illustrates a DR imaging system 1200 using the arrangement of DR detectors as described in relation to FIG. 9 and FIG. 11 for use in a long-length imaging exposure. DR detector 1201 may comprise a wired or wireless DR detector of the type 600 described in relation to FIG. 6; DR detector 1202 may comprise a wired or wireless standard DR detector type of the type 400 described in relation to FIG. 4; and DR detector 1203 may comprise another wired or wireless DR detector of the type 600. X-ray source 501 may be fired once to expose a subject (not shown) to an x-ray beam 16 when the subject is placed between the x-ray radiation source 501 and the multiple DR detectors 1201-1203, to capture a distributed image of the subject that is simultaneously captured and stored by the multiple DR detectors 1201-1203. The captured images, each comprising a portion of the subject, one from each DR detector, may be stitched together using known computer implemented reconstruction techniques to generate a single long-length composite image of the subject. Part of the control operations carried out by the image processing and control unit 34 may include wired or wireless communication with the DR detectors 1201-1203 for verification that the DR detectors have been initiated and are all in a ready state before exposure, for synchronization, and for coordinating storage and identification of image frame data from each of the detectors. Such a method does not require time consuming repositioning of one or more DR detectors 1201-1203, as well as not requiring repositioning of the x-ray source 501, or multiple exposures, as may be currently practiced to obtain a long-length radiographic image. The arrangement of DR detectors 1201-1203 may be configured by attachment to a rigid structure 1200 using a modified "bucky" arrangement to fix in position each of the DR detectors 1201-1203, or the detectors 1201-1203 may be affixed to a wall. Alternatively, the DR detector 1202 may be part of an existing permanent radiographic imaging installation which is fixed in position as shown, while the other two DR detectors 1201, 1203, may be portable (temporarily fixed) DR detectors. One embodiment of the present invention may comprise a retrofittable separate structure for temporarily securing in position the DR detectors 1201 and 1203 as shown and allowing movement of the structure having these two detectors 1201, 1203, to position them in front of (overlapping) the fixed installation of DR detector 1202, as will be described below in relation to FIG. 12B. Although the arrangement of DR detectors 1201-1203 has been illustrated as a vertical alignment wherein the imaging planes of the DR detectors are vertical, it should be noted that any of the tiled arrangements of DR detectors disclosed herein may be positioned in a substantially horizontal alignment wherein the imaging planes of the DR detectors are horizontal, such as may be used for a human patient who is lying down on an examination bed with an x-ray source positioned above the patient, or the DR detectors disclosed herein may be positioned in a substantially horizontal alignment wherein the imaging planes of the DR detectors are vertical.

FIG. 12B illustrates a DR imaging system 1250 using an arrangement of DR detectors as described in relation to FIG. 12A for use in a long-length imaging exposure, except that the DR detectors 1201, 1203, are affixed to a transport apparatus 1251 comprising a support post 1254 attached to a base 1256 outfitted with means for transporting the apparatus 1251 and DR detectors 1201, 1203, such as wheels 1257 which may include freely rotatable wheels, lockable wheels, wheels that may be lowered or raised by hand cranking or by electric motor under operator control, wheels that are not motor-assisted, and motor driven wheels that may be powered by an electric motor to assist in manually transporting the apparatus 1251. The support post 1254 secures in vertical relative position the DR detectors 1201, 1203 with a preselected gap size therebetween 1255 sufficient for the respective bottom and top edges of the DR detectors 1201, 1203, to overlap a top and bottom edge of DR detector 1202, as previously described. As mentioned above, the DR detector 1202 may represent a standard prior art DR detector permanently installed on one wall 1252 such as in a medical facility imaging room. The DR detector 1202 may be used alone with x-ray source 501 for standard non-elongated radiographic imaging and, in the case where a long-length radiographic image may be desired, the apparatus 1251 may be rolled into position 1260 along a floor of an imaging room. Similarly, DR detectors 1201, 1203, may be usable individually for performing standard radiographic imaging of patients and may be inserted or attached to support post 1254 to configure the transport apparatus 1251 as described herein. Thus, the transportable pair of DR detectors 1201, 1203, may be advantageously affixed to the transport apparatus 1251 to provide a capability to easily convert the permanent installation of the standard DR detector 1202 into the long-length imaging system 1250 when combined as shown with two new modified DR detectors of the type 600 each having one or more edges being radiolucent.

As before, x-ray source 501 may be fired once to expose a subject (not shown) when the subject is placed in front of the multiple DR detectors 1201-1203. Part of the control operations carried out by the image processing and control unit 34 may include wired or wireless communications, wherein wireless communications are represented as wireless transmission signals 1258, with the DR detectors 1201-1203, such as waiting for and synchronizing ready state signals from all activated DR detectors 1201-1203 before an exposure by x-ray source 501. Such a method does not require time consuming repositioning of one or more DR detectors 1201-1203, as well as not requiring repositioning of the x-ray source 501, or multiple exposures, as may be currently practiced to obtain a long-length radiographic image.

Figure 13:
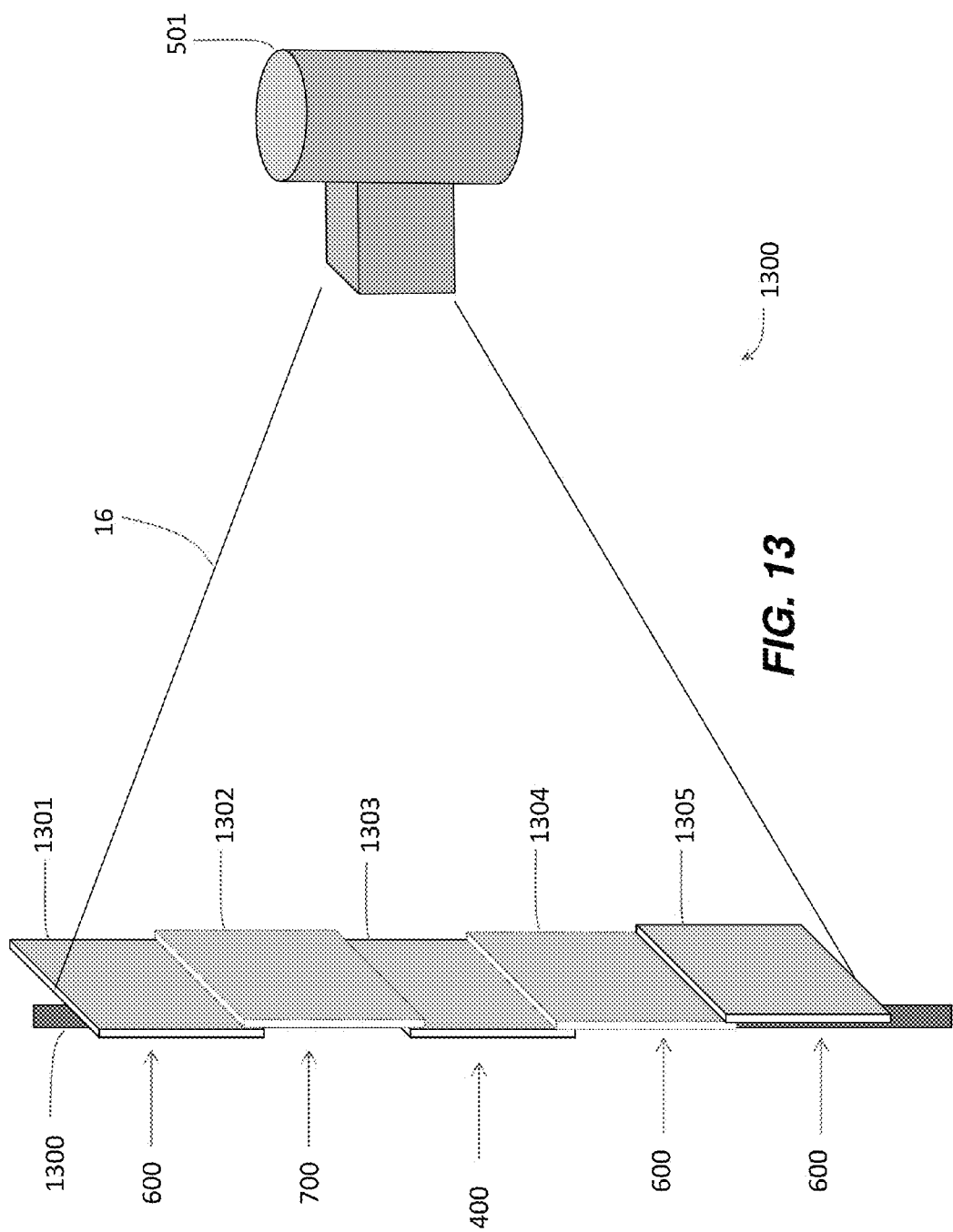
FIG. 13 is a perspective view of an imaging system implementing an arrangement of DR detectors according to one embodiment.

FIG. 13 illustrates an embodiment of a DR imaging system 1300 wherein more than three DR detectors are positioned in an overlapping fashion to capture a long-length radiographic image. X-ray source 501 may emit a single radiographic energy pulse that is received and captured by DR detectors 1301-1305 as shown. A subject positioned in front of the DR detectors 1301-1305 may result in radiographic images being generated in the DR detectors 1301-1305, each comprising a portion of a radiographic image of the subject using the single radiographic energy pulse. As shown, DR detector 1301, the uppermost DR detector as shown, is illustrated as a DR detector 600 as described herein with reference to FIG. 6. Because DR detector 1301 is not positioned forward of another DR detector, it may alternatively comprise a standard DR detector such as the DR detector 400 described in relation to FIG. 4. Moreover, DR detector 1301 may comprise a DR detector such as the DR detector 700 described in relation to FIG. 7. Such alternate configurations are considered to be encompassed by the present disclosure because they embody preferred configurations wherein a radio-opaque edge of any DR detector used does not overlap the imaging array of another DR detector positioned behind it. In similar fashion, DR detector 1302, second from the top as shown, may comprise a detector of the type described in relation to FIG. 7 wherein opposite edges (top and bottom edges in the perspective of FIG. 13) are configured to be radiolucent; DR detector 1303, third from the top as shown, may comprise a standard DR detector 400 of the type described in relation to FIG. 4, or it may comprises a DR detector 600 or 700 as described in relation to FIG. 6 and FIG. 7, respectively; DR detector 1304, fourth from the top as shown, may comprise a DR detector 600 as described in relation to FIG. 6 wherein only its upper edge is configured to be radiolucent; and DR detector 1305, at the bottom of the arrangement as shown, may similarly comprise a DR detector 600 as described in relation to FIG. 6 wherein only its upper edge is configured to be radiolucent. The detectors 1303-1305 are positioned in a staggered stepwise arrangement, which stepwise arrangement may comprise an alternative arrangement for all the DR detectors 1301-1305, as desired. As shown, the DR detectors 1301-1305 may be fixed to a support structure 1300 for securing in position the DR detectors 1301-1305.

As will be appreciated by one skilled in the art, aspects of the present invention may be embodied as a system, an apparatus, and a method, for capturing long length images of a subject using multiple DR detectors.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A digital radiographic detector comprising:
a housing comprising a top side, a bottom side substantially parallel to the top side, and a plurality of edges extending between a periphery of the top side and a periphery of the bottom side to form an interior volume of the housing; and
a multilayer imaging structure within the interior volume of the housing, the multilayer imaging structure comprising a substantially planar imaging side configured to face the top side of the housing and to face an external radiographic energy source emitting radiographic energy toward the top side of the housing,
wherein the top side of the housing comprises a radiolucent material, at least one of the plurality of edges of the housing is made from a radiolucent material, and wherein at least one of the plurality of edges of the housing is made from a radiopaque material.

2. The detector of claim 1, wherein the multilayer imaging structure further comprises:
an imaging device layer to receive light energy; and
a scintillator layer adjacent the device layer, the scintillator layer to convert the radiographic energy to the light energy.

3. The detector of claim 2, wherein the top side of the housing is sealingly attached to the at least one of the plurality of edges of the housing made from the radiopaque material.

4. The detector of claim 3, wherein the bottom side of the housing comprises a radiopaque material, the bottom side of the housing is sealingly attached to the at least one of the plurality of edges of the housing made from the radiolucent material.

5. The detector of claim 2, further comprising a scanning circuit, a read-out circuit, and a bias circuit all enclosed within the interior volume of the housing and in electrical communication with the imaging device layer.

6. The detector of claim 2, further comprising a transmitter for wirelessly communicating with an image control processing system and for wirelessly transmitting a ready signal to the image control processing system.

7. A digital radiography system comprising:
an x-ray source configured to emit x-rays;
a first DR detector comprising:
    a housing comprising a top side, a bottom side substantially parallel to the top side, and a plurality of edges extending between a periphery of the top side and a periphery of the bottom side to form an interior volume of the housing; and
    a multilayer structure within the interior volume of the housing, the multilayer structure comprising a substantially planar imaging side configured to face the top side of the housing and to face the x-ray source emitting the x-rays toward the top side of the housing, an imaging device layer to receive light energy, and comprising a scintillator layer adjacent the device layer, the scintillator layer to convert the x-rays to the light energy,
    wherein the top side of the housing comprises a radiolucent material, and wherein two opposing parallel edges of the plurality of edges of the housing are made from a radiolucent material;
and
second and third DR detectors each positioned behind one of the two opposing parallel edges of the first DR detector with respect to the x-ray source and each comprising a radiopaque housing without radiolucent edges.

8. The system of claim 7, wherein the top side of the housing comprises an outermost top surface of the first DR detector.

9. The system of claim 8, wherein the top side of the housing extends continuously to form the two opposing parallel edges of the plurality of edges of the housing made from the radiolucent material.

10. The system of claim 7, further comprising an image acquisition control system configured to wirelessly communicate with the first, second, and third DR detectors and to wirelessly receive a ready signal from each of the first, second, and third DR detectors before activating the x-ray source.

11. A long-length imaging system comprising:
first and second DR detectors, each comprising:
    a housing comprising a top side, a bottom side substantially parallel to the top side, and a plurality of edges extending between a periphery of the top side and a periphery of the bottom side to form an interior volume of the housing; and
    a multilayer structure within the interior volume of the housing, the multilayer structure comprising a substantially planar imaging side configured to face the top side of the housing, an imaging device layer to receive light energy, and comprising a scintillator layer adjacent the device layer, the scintillator layer to convert radiographic energy to the light energy,
    wherein the top side of the housing comprises a radiolucent material, and wherein only one edge of the plurality of edges of the housing is made from a radiolucent material;
and
a third DR detector disposed behind the first and second DR detectors, such that said only one radiolucent edge of the first and second DR detectors each overlaps a different parallel edge of the third DR detector, the overlapped edges of the third DR detector comprising radiopaque edges.

12. The system of claim 11, further comprising a transportable support structure securing in a vertical relative position the first and second DR detectors with a preselected gap size therebetween.

13. The system of claim 12, wherein the transportable support structure comprises means for moving the transportable support structure such that the first and second DR detectors are simultaneously positioned forward of the third DR detector.

14. The system of claim 13, wherein the means for moving the transportable support structure comprises wheels powered by an electric motor.

15. The system according to claim 11, further comprising an x-ray source, and wherein the system is configured to capture a portion of a radiographic image of a subject on each of the first, second, and third DR detectors simultaneously using one exposure by the x-ray source.

16. The system of claim 15, wherein the preselected gap size is large enough for the third DR detector to be exposed by the one x-ray exposure.

17. The system of claim 15, further comprising an image acquisition control system configured to wirelessly communicate with each of the first, second, and third DR detectors and to wirelessly receive a ready signal from each of the first, second, and third DR detectors before activating the x-ray source.

18. The system of claim 15, wherein the third DR detector is a non-portable DR detector fixed in a stationary position, and wherein the first and second DR detectors are each a portable independently usable DR detector.

19. The system of claim 11, wherein the first, second and third detectors are disposed along a horizontal axis.

* * * * *